(12) United States Patent
Li et al.

(10) Patent No.: US 7,910,074 B2
(45) Date of Patent: Mar. 22, 2011

(54) SYSTEM AND METHOD FOR CONTINUOUSLY TRANSFERRING AND PROCESSING LIQUIDS

(75) Inventors: William W. Li, Miami, FL (US); Rongchang Xin, Miami, FL (US); Elgardo Echevarria, Miami, FL (US); John A. Mitchell, Miami, FL (US)

(73) Assignee: Beckman Coulter, Inc., Fullerton, CA (US)

(*) Notice: Subject to any disclaimer, the term of this patent is extended or adjusted under 35 U.S.C. 154(b) by 1181 days.

(21) Appl. No.: 11/249,192

(22) Filed: Oct. 13, 2005

(65) Prior Publication Data
US 2007/0086923 A1 Apr. 19, 2007

(51) Int. Cl.
*B01L 3/02* (2006.01)
(52) U.S. Cl. ..... 422/518; 422/100; 436/180; 73/863.71; 73/863.73; 261/19; 261/20; 261/21; 261/22; 222/61; 222/62
(58) Field of Classification Search .......... 422/100; 436/180; 222/61–62; 383/80; 261/19–22; 73/863.71, 863.73; 220/246, 253, 366.1, 220/367.1, 203.1, 203.23, 348, 580; 215/200, 215/272, 293, 294, 306, 307, 315, 316, 321, 215/342–345, 282, 287; 160/44
See application file for complete search history.

(56) References Cited

U.S. PATENT DOCUMENTS

| | | | | |
|---|---|---|---|---|
| 107,449 A * | 9/1870 | Clark et al. | ..................... | 215/283 |
| 2,760,367 A * | 8/1956 | Stromberg | ........................ | 73/40 |
| 2,847,851 A * | 8/1958 | Enell | ................................. | 73/40 |
| 3,035,436 A * | 5/1962 | Johnson | ........................... | 73/40 |
| 3,243,071 A * | 3/1966 | Kimmel | ......................... | 215/260 |
| 3,255,631 A * | 6/1966 | Franks | ........................... | 374/143 |
| 3,313,144 A * | 4/1967 | Johnson | ........................ | 73/49.7 |
| 3,349,954 A * | 10/1967 | May | ............................. | 220/86.2 |
| 3,358,871 A * | 12/1967 | Leichner | .................. | 141/311 R |
| 4,056,120 A * | 11/1977 | MacNeilage | .............. | 137/493.9 |
| 4,070,156 A | 1/1978 | Moran et al. | | |
| 4,601,409 A | 7/1986 | DiRegolo | | |
| 4,634,017 A * | 1/1987 | Kilayko | .................. | 220/203.23 |
| 4,667,507 A * | 5/1987 | Eriksson | ........................ | 73/49.7 |
| 4,679,424 A * | 7/1987 | Tubman | ........................ | 73/45.8 |
| 4,691,836 A * | 9/1987 | Wassilieff | ..................... | 215/298 |
| 4,809,542 A * | 3/1989 | Jones | ............................. | 73/45.8 |
| 5,027,978 A * | 7/1991 | Roeser | ............................ | 222/63 |
| 5,069,062 A * | 12/1991 | Malecek et al. | ................ | 73/49.7 |
| 5,105,653 A * | 4/1992 | Konter | ........................... | 73/49.2 |
| 5,324,114 A * | 6/1994 | Vinci | ............................. | 374/208 |

(Continued)

Primary Examiner — Jill Warden
Assistant Examiner — Shogo Sasaki
(74) Attorney, Agent, or Firm — Sterne, Kessler, Goldstein & Fox PLLC

(57) ABSTRACT

A liquid transfer system for transferring liquid from a plurality of containers to a plurality of destinations comprises a plurality of inlet valves. Each inlet valve is operable between an open position allowing liquid from a container to be drawn into the system and a closed position blocking liquid from a container from being drawn into the system. Liquid drawn from each of the liquid containers is delivered to a buffer chamber designed to degas the liquid in the buffer chamber. The buffer chamber leads to a vented feeder chamber that is also adapted to retain a volume of liquid. A chamber connection valve is provided between the buffer chamber and the feeder chamber to allow or block the flow of liquid between the buffer chamber and the feeder chamber. The feeder chamber is connected to a plurality of distribution valves operable to deliver liquid to a plurality of destinations.

19 Claims, 6 Drawing Sheets

U.S. PATENT DOCUMENTS

| | | |
|---|---|---|
| 5,488,447 A | 1/1996 | Patton et al. |
| 5,630,935 A * | 5/1997 | Treu .............................. 210/130 |
| 5,652,937 A | 7/1997 | Earle et al. |
| 5,758,700 A * | 6/1998 | Vanderploeg ................. 141/347 |
| 6,202,717 B1 * | 3/2001 | Markey et al. ................ 141/383 |
| 6,675,987 B2 | 1/2004 | Soberunie et al. |
| 6,767,188 B2 | 7/2004 | Vrane et al. |
| 7,222,742 B2 * | 5/2007 | Liao ........................... 220/367.1 |
| 2003/0189051 A1 * | 10/2003 | Liu ................................ 220/303 |
| 2003/0215957 A1 | 11/2003 | Lemmo et al. |
| 2004/0014238 A1 | 1/2004 | Krug et al. |

* cited by examiner

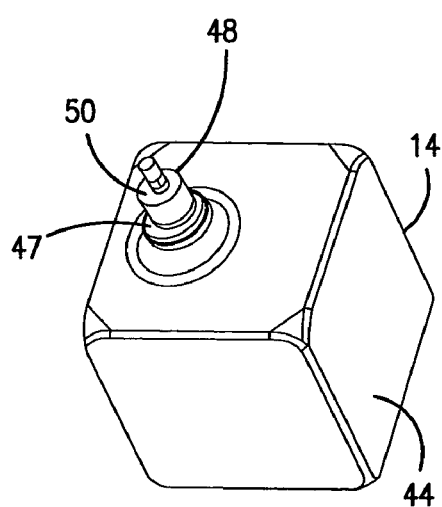 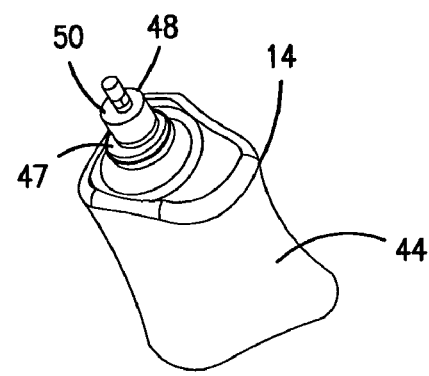
FIG. 3A  FIG. 3B

SYSTEM AND METHOD FOR CONTINUOUSLY TRANSFERRING AND PROCESSING LIQUIDS

BACKGROUND

This invention relates to the field of liquid transfer and processing systems, and more particularly to liquid transfer and processing systems used for chemistry analysis, including chemistry analysis in the field of hematology.

In hematology and other fields of chemistry analysis, a chemical in the form of a liquid reagent often needs to be delivered to several consuming stations. For example, in the field of hematology, a reagent in the form of a dilution liquid often needs to be simultaneously delivered to a complete blood cell counting mixing chamber, a differential white cell count mixing chamber, and a reticulocyte count mixing chamber. At other times, several different liquid reagents may need to be delivered to a single consuming station. For example, in the field of hematology, lyse and stabilyse are delivered to a single white cell differential count mixing chamber to break down the red blood cells. After the liquid reagents are delivered, a cleaning liquid may be delivered through the system and to the consuming stations to cleanse the system for a new analysis.

In most existing liquid reagent transfer systems, each different liquid reagent has its own transfer system used to distribute the liquid reagent. When multiple reagents are used, multiple reagent transfer systems must be used to deliver the reagents from location to location. Multiple reagent transfer systems result in increase system costs to the user. In addition, the numerous reagent transfer systems consume a great deal of valuable laboratory space. In addition, these systems are inefficient in terms of reagent consumption, as reagents remain in each of the multiple transfer systems following a laboratory run, and the left over reagents must be cleansed from each of the multiple systems. Over time, the volume of reagents cleansed from multiple systems becomes substantial, resulting in a significant waste of resources and significant costs to the user in terms of wasted reagents. Accordingly, it would be desirable to provide an efficient liquid chemical transfer and processing system capable of transferring multiple liquids from multiple locations and delivering such liquids and/or liquid combinations to multiple locations.

In many prior art liquid transfer systems, a pick-up assembly is attached to each reagent container. The pick-up assemblies are designed to remove reagents from the containers and deliver them to transfer tubes, which distribute the reagents throughout the system. Unfortunately, these pick-up assemblies often cause contamination of the reagent going into the system. Pick-up assemblies that have surfaces extending in the reagent are particularly susceptible to this problem. However, nearly all pick-up assemblies are susceptible to the problem of introducing small air bubbles into the system (i.e., "micro gas bubbles") when little reagent remains in the container. The introduction of micro gas bubbles into the system often results in false readings from system measuring instruments. Accordingly, it would be desirable to provide a liquid transferring system capable of reducing the amount of micro gas bubbles introduced into the system and/or eliminating micro gas bubbles from liquids before such liquids are subjected to measuring instruments of the system.

Another problem with many prior art liquid transfer and processing systems is that laboratory runs must be temporarily stopped when a volume of reagent is consumed from the container holding the reagent. In particular, when a reagent container is emptied, the laboratory run must be temporarily stopped to allow a full reagent container to be connected to the system. These delays in laboratory testing waste valuable time and resources. Accordingly, it would be further advantageous to provide a system capable of continuously supplying a liquid reagent to one or more consuming stations, in order for a laboratory process to continue for as long as needed without the need for temporary delays in the laboratory run to replace spent reagent containers.

SUMMARY OF THE INVENTION

A liquid transfer system for transferring liquid from at least one container to at least one destination comprises an inlet manifold including a plurality of inlet valves. Each of the inlet valves is connected to a cap adapted to seal to a liquid container. Each inlet valve is operable between an open position allowing liquid from an associated container to be drawn into the system and a closed position blocking liquid from an associated container from being drawn into the system. Liquid drawn from each of the liquid containers passes through the inlet manifold and on to a first chamber adapted to retain a volume of liquid. The first chamber is a buffer chamber designed and adapted to degas the liquid in the buffer chamber. The buffer chamber includes a liquid outlet port and a liquid inlet port connected to the inlet manifold. A lid is provided on the first chamber. The lid includes a pressure port operable to subject the first chamber to a pressure and a vacuum port operable to subject the first chamber to a vacuum.

The outlet port of the first chamber leads to a second chamber that is also adapted to retain a volume of liquid. A chamber connection/bridge valve is provided between the first chamber and the second chamber to control the flow of liquid between the first chamber and the second chamber. The second chamber is a vented feeder chamber designed and adapted to deliver liquid to a plurality of consuming stations. The feeder chamber includes an inlet port connected to the outlet port of the first chamber. The feeder chamber also includes an outlet port connected to a distribution manifold. The distribution manifold includes a plurality of distribution valves. Each distribution valve is operable between an open position and a closed position. In the open position, liquid from the system is allowed to pass to an associated consuming station destination. In the closed position, liquid from the system is blocked from passing to the associated consuming station destination.

Both the first chamber and the second chamber include sensors operable to determine the level of liquid within the chamber. Each sensor generally comprises a low level sensor operable to determine if the liquid in the chamber is above a low level and a full level sensor operable to determine if the liquid in the chamber is above a high level.

The system further includes a microcontroller operable to receive a plurality of input signals and deliver a plurality of output signals. The plurality of input signals include signals from the low level sensors and the high level sensors. The plurality of output signals include inlet valve control signals, distribution valve control signals, a vacuum control signal and a pressure control signal.

In one embodiment, the caps connected to each of the plurality of liquid containers comprise a cap body including an upper portion with an aperture and at least one depending skirt. A plunger passes through the aperture in the upper portion of the cap body. The plunger includes a head portion connected to a cylindrical shaft, with the cylindrical shaft connected to a lower plate portion. The lower plate portion is disc shaped and includes an upper surface and a bottom surface. A spring is positioned between the upper portion of the cap body and the upper surface of the lower disc portion of the plunger such that the spring biases the lower disc portion of the plunger away from the upper portion of the cap. A gasket is connected to the bottom surface of the lower portion of the plunger to provide a seal between the cap and the container.

In one embodiment the foregoing system is placed in operation by using the caps to seal the liquid input line to a plurality of containers. Next, the controller opens the appropriate inlet valve or valves and a vacuum is applied to the first chamber, thereby aspirating liquid from at least one container to the first chamber through the liquid input line. As liquid is aspirated into the first chamber, gasses are drawn out of the first chamber using the vacuum applied to the first chamber. When liquid in the first chamber is to be transferred to the second chamber, the bridge valve is opened and a pressure is applied to the first chamber. The pressure in the first chamber thus forces liquid from the first chamber to the second chamber. The liquid in the second chamber may then be distributed to at least one of the plurality of destinations.

BRIEF DESCRIPTION OF DRAWINGS

FIG. 3A is a perspective view of a filled liquid container for use in the system of FIG. 1;

FIG. 3B is a perspective view of the liquid container of FIG. 3A with the liquid substantially depleted from the container;

DESCRIPTION OF THE BEST MODE OF THE INVENTION

Figure 1:
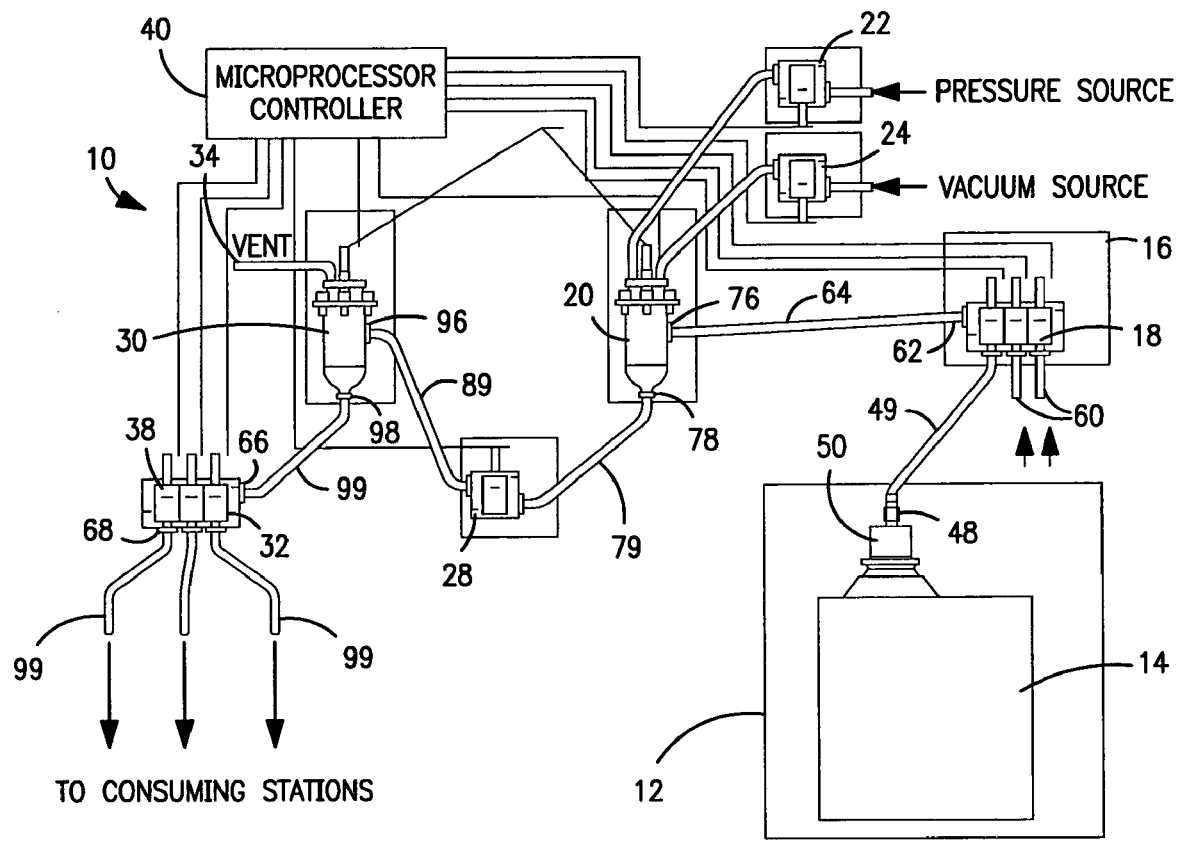
FIG. 1 shows a schematic representation of a system for continuously transferring and processing liquids.

With reference to FIG. 1, a system 10 for continuously transferring and processing liquids comprises a reagent station 12 comprising at least one liquid container 14. The at least one liquid container 14 is attached to an inlet manifold 16 comprising a plurality of inlet valves 18. The inlet manifold 16 leads to a buffer chamber 20. The buffer chamber 20 is connected to a pressure source through a pressure valve 22 and to a vacuum source through a vacuum valve 24. The outlet 78 of the buffer chamber 20 leads to a vented feeding chamber 30. A bridge valve 28 is positioned between the buffer chamber 20 and the feeding chamber 30 and is operable to allow or block liquid flow between the buffer chamber 20 and the feeding chamber 30. The outlet of the feeding chamber 30 leads to a distribution manifold 32. The distribution manifold 32 is connected to at least one liquid consuming station. A microprocessor controller 40 (also referred to herein as a "microcontroller" or "controller") is connected to several of the above-described components. The controller 40 is operable to deliver control signals to each of such components. The controller 40 may also be connected to a master system controller and receive instructions and report status to the master system controller.

The reagent station 12 typically comprises a plurality of liquid containers 14 filled or partially filled with liquid reagents. Although only one liquid container 14 is shown in FIG. 1, the system contemplates as many liquid containers as inlet valves 18. Furthermore, although only three inlet valves 18 are shown in FIG. 1, one of ordinary skill in the art will recognize that any number of inlet valves 18 and associated containers 14.

An exemplary liquid container 14 is shown in FIG. 3A. Each container includes a flexible/deformable body portion 44. The body portion may be comprised of a rubber or a flexible plastic material impervious to liquid. A neck 47 leading to a mouth is provided in each liquid container 14 near the top of the body portion 44. The mouth defines an opening to the interior of the container 14, and allows for liquid passage out of the container 14. The neck 47 is configured to receive a cap. When the containers 14 are stored, a storage cap is used to seal off the interior of the container 14 and prevent the escape of liquid from the container. A pick-up cap 50 is used when the container 14 is connected to the system 10. These pick-up caps 50 each include an aperture to allow liquid to pass from the container 14 and into a tube connected to the cap. To this end, the cap 50 includes a tube fitting 48 designed to join the tube to the cap 50. One embodiment of a cap 50 that is particularly useful with the system 10 described herein is shown with reference to FIGS. 4A and 4B and described in further detail below. Each cap 50 is designed to seal to the mouth 46 of the container 14 to prevent air from entering into the container and/or the tube connected to the cap 50 as liquid is aspirated or otherwise drawn from the container 14.

With reference now to FIG. 3A, the body portion 44 of each liquid container 44 is generally block shaped when filled with liquid. As liquid is drawn from the container 14, the body portion 44 of the flexible container collapses, as shown in FIG. 3B. A vacuum is generally used to draw liquid out of the container. Because the cap 50 is sealed to the mouth of the container 14, when the vacuum draws the liquid from the container, the vacuum also causes the container to nearly completely collapse upon itself. In one advantageous embodiment, the containers 14 are placed in the reagent station 12 with the necks 47 in a downward position. This allows gravity to assist in bringing nearly all of the liquid within the container 14 to the cap 50, as the last bit of liquid is drawn from the container. Because the flexible containers 44 collapse, a user of the system has a clear indication when little liquid remains in the container. This provides an indication to the user that the spent container should be replaced with a new container. In another embodiment, a sensor is included in the cap 50 to indicate when liquid is nearly exhausted from the container.

Returning again to FIG. 1, each container 14 is connected to the inlet manifold 16 by a liquid input line in the form of a section of flexible plastic tubing 49. The manifold 16 includes a plurality of inlet ports 60 and a single outlet port 62. Each section of plastic tubing 49 leads to a container 14 and extends between a cap fitting 48 on the container 14 and one of the inlet ports 60. Each inlet port 60 leads to one of the plurality of inlet valves 18. Each inlet valve 18 is operable to open or close the associated inlet port 60, thereby enabling the passage of liquid or blocking the passage of liquid through the port 60. The controller 40 is connected to each of the plurality of inlet valves 18 and is operable to deliver control signals to the inlet valves in order to open or close the valves. Each inlet valve 18 leads to the outlet port 62 of the inlet manifold 16. Another section of flexible tubing 64 of the liquid input line extends between the outlet port 62 and the buffer chamber 20. Application of a vacuum to the tubing 64 draws liquid from the containers 14 that are connected to open inlet ports 18 of the inlet manifold 16. Liquid drawn from the containers 14 moves through the inlet manifold 16, down the tubing 64 and to the buffer chamber 20.

Figure 2:
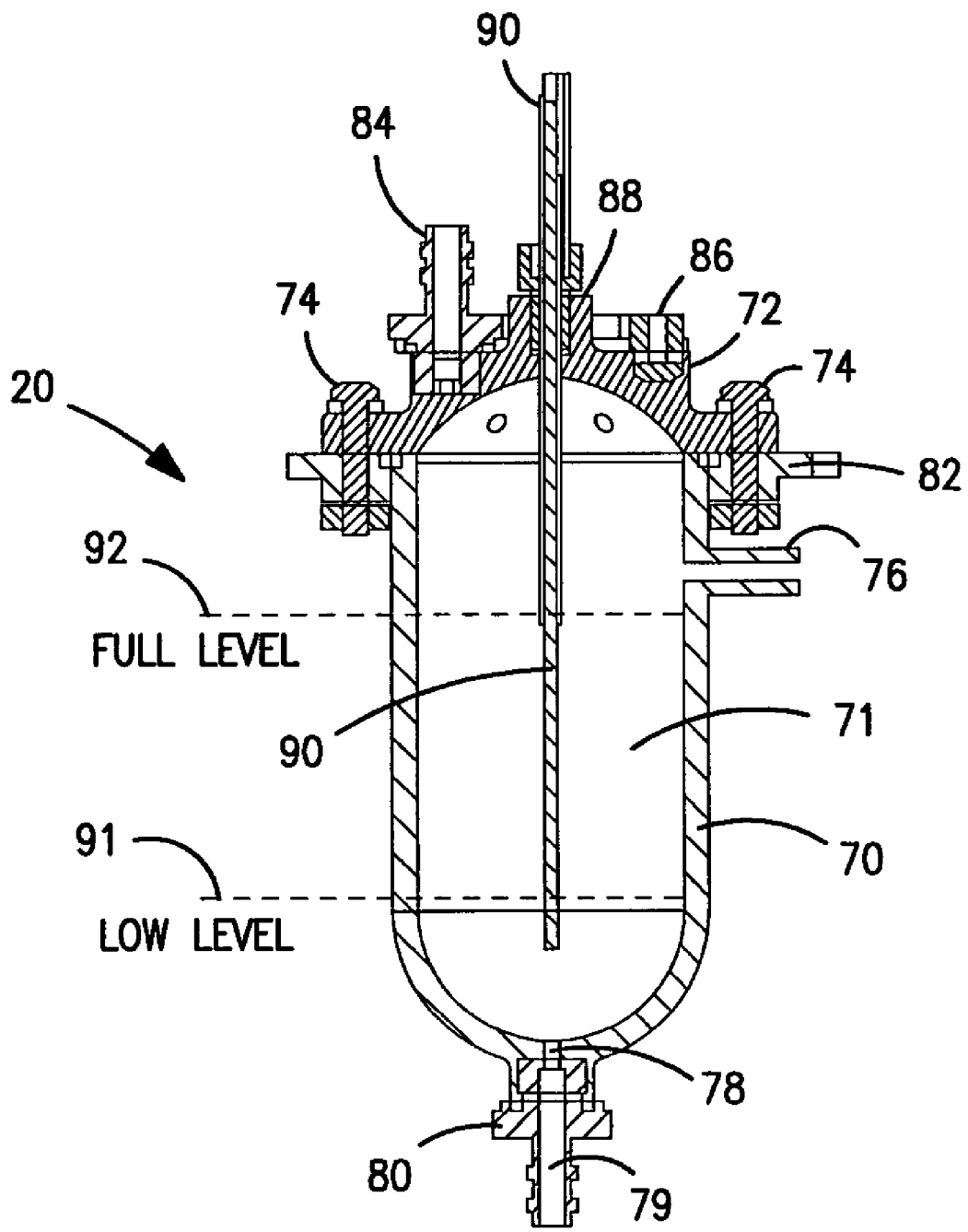
FIG. 2 is a side cross-sectional view of a chamber assembly for use in the system of FIG. 1.

With reference now to FIG. 2, the buffer chamber 20 includes a body portion 70 and a lid 72 connected to the body portion 70. The body portion 70 generally defines an interior portion/reservoir 71 of the first liquid container 20. The reservoir 71 is designed to hold about 40 ml to 100 ml of liquid. An outlet port 78 is formed in the body 70 at or near the bottom portion of the body. The outlet port 78 is an opening in the body that allows liquid to pass from the reservoir 71 and into a section of flexible tubing 79 connected to the outlet port 78. A fitting 80 is provided to secure the tubing 79 to the outlet port 78. The body portion 70 of the buffer chamber 20 also includes an inlet port 76. The inlet port 76 provides a passage into the interior reservoir 71 of the buffer chamber. The inlet port 76 is designed to receive the flexible portion of tubing 64 connected to the inlet manifold 16, and allow liquid to pass from the tubing to the interior reservoir 71 of the buffer chamber 20. The body portion 70 of the buffer chamber further includes a top rim 82 defining the top of the interior reservoir 71.

The lid 72 of the buffer chamber is designed to fit on the rim 82 of the body portion 70 and seal to the body portion 70. Nut and bolt assemblies 74 may be used to secure the lid 72 to the rim 82 of the body portion 70. In one embodiment a seal, such as a gasket, is provided between the lid and the body portion. For example, an O-ring type seal may be used to provide an air-tight fit between the lid 72 and the rim 82 of the body portion. In another embodiment, the lid 72 and rim 82 may be sufficiently smooth to provide an air-tight seal without the use of an O-ring or other seal.

The lid 72 further includes a plurality of passages to provide communication into the interior reservoir 71 of the buffer chamber 20. For example, the lid 72 includes a pressure port 84 and a vacuum port 86. The pressure port 84 of the lid 72 is connected to flexible tubing that extends to a pressure valve 22, as shown in FIG. 1. The pressure valve 22 leads to a pressure source. In one embodiment, the pressure source delivers inert gas to the interior portion 71 of the buffer chamber 20 through the pressure valve 22 and pressure port 84. The inert gas is delivered to the buffer chamber 20 at an increased pressure, generally causing the pressure in the buffer chamber to exceed atmospheric pressure. An electrical lead extends between the pressure valve 22 and the microcontroller 40. This electrical lead allows the microcontroller 40 to provide control signals to the pressure valve 22 and thereby control whether the buffer chamber 20 is subjected to the pressure source. In particular, if the microcontroller 40 instructs the pressure valve 22 to open, the buffer chamber 20 is subjected to the pressure source. However, when the microcontroller 40 instructs the pressure valve 22 to close, the buffer chamber 20 is isolated from the pressure source.

The vacuum port 86 of the lid 72 is connected to flexible tubing that extends to a vacuum valve 24, as also shown in FIG. 1. The vacuum valve 24 leads to a vacuum source. The vacuum valve 24 is operable between an open position and a closed position. In the open position, the vacuum source subjects the internal portion 71 of the buffer chamber to a vacuum. However, in the closed position, the vacuum valve 24 blocks the internal portion 71 of the buffer chamber 20 from the vacuum source. An electrical lead connects the microcontroller 40 to the vacuum valve 24, allowing the microcontroller 40 to provide control signals to the vacuum valve 24 and thereby control operation of the vacuum valve between the open and closed positions.

As shown in FIG. 2, the lid also includes a sensor port 88. A liquid level sensor 90 passes through the sensor port 88 such that one end of the liquid level sensor 90 is outside of the buffer chamber 20 and another end of the liquid level sensor extends into the internal reservoir 71. The liquid level sensor is operable to determine the level of liquid within the internal reservoir 71 and generate a sensor signal for delivery to the microprocessor controller 40. In particular, the liquid level signal is operable to generate a "low" signal when the level of liquid within the buffer chamber is below a low level 91 and generate a "full" signal when the level of liquid within the buffer chamber is above a full level 92. An electrical lead extends between the controller 40 and the external end of the liquid level sensor 90 to allow the signal generated by the liquid level sensor to be delivered to the controller. In one embodiment, the level sensor 90 includes two sensing elements. In this embodiment, the status of the buffer chamber 20 is "full" when both sensing elements are immersed in liquid. The status of the buffer chamber is "normal" when the top element is off the liquid and the bottom element is in the liquid. The status of the buffer chamber is "low" when both elements are off the liquid. Accordingly, the controller 40 is continually provided with information about the level of liquid within the buffer chamber 20.

With reference again to FIG. 1, the outlet port 78 of the buffer chamber 20 is connected to a bridge valve 28 via the section of flexible tubing 79. The bridge valve 28 is also connected to the feeding chamber 30 via another section of flexible tubing 89. The bridge valve is operable between an open position and a closed position. In the open position, liquid from the buffer chamber 20 is allowed to pass through the bridge valve 28 and to the feeding chamber 30. In the closed position, the bridge valve 28 blocks liquid from passing from the buffer chamber 20 to the feeding chamber 30. The bridge valve 28 is electrically connected to the controller 40. The controller 40 is operable to deliver control signals to the bridge valve 28 to control operation of the bridge valve between the open and the closed positions.

The feeding chamber 30 is similar to the buffer chamber 20 shown in FIG. 2. In particular, the feeding chamber includes a body portion 70 with an inlet port 96 and an outlet port 98. The body portion 70 of the feeding chamber 30 defines an interior/reservoir portion 71 designed to hold about 40 ml to 100 ml of liquid. The body portion 70 of the feeding chamber also includes a rim 82 and the lid 72 of the feeding chamber rests on the rim. However, unlike the lid of the buffer chamber 20, the lid of the feeding chamber 30 does not include a pressure port 84 or a vacuum port 86. Instead, the lid of the feeding chamber 30 includes a vent 34. The vent 34 is simply an opening in the lid which provides a passage from the internal portion 71 of the second liquid chamber 30 to the open air outside of the system. Accordingly, the pressure within the feeder chamber is generally atmospheric pressure. Because neither a vacuum nor pressure is applied to the feeding chamber 30, the lid may or may not be sealed to the body portion.

A level sensor is mounted to the lid of the feeding chamber 30 and extends into the internal portion of the feeding chamber 30. The level sensor is connected to the controller 40 and is operable to determine whether the level of liquid within the feeding chamber 30 is above a full level or below a low level. If the level of liquid is above the full level, the level sensor provides a "full" signal to the controller. If the level of liquid is below the low level, the level sensor provides a "low" signal to the controller.

The outlet port 98 of the feeding chamber is connected by flexible tubing 99 to a distribution manifold 32. The distribution manifold 32 includes an inlet port 66 connected to a plurality of outlet ports 68. A distribution valve 38 is positioned at each outlet port 68. Each distribution valve 38 is operable between an opened and closed position. In the open position, the distribution valve 38 allows liquid to flow through the distribution valve 38 and its associated outlet port 68. In the closed position, the distribution valve 38 blocks liquid from flowing through the distribution valve 38 and its associated outlet port 68. A plurality of flexible tubes 99 are connected to the plurality of outlet ports 68. The plurality of flexible tubes 99 lead to measurement apparatus and/or other consuming stations designed to receive the liquid reagents transferred from the containers 14 and processed by the system 10.

Operation of the system is now described with reference to FIGS. 1 and 5. First, in step 202 of FIG. 5, the controller 40 is provided with instructions concerning the appropriate liquid or liquid mixture to be processed using the system. This allows the controller 40 to open the inlet valve or valves in the inlet manifold 16 that correspond to the desired liquid or liquid combination. In one embodiment of the system, each inlet valve 18 corresponds to a different type of liquid. In a second embodiment of the system, each inlet valve 18 corresponds to the same type of liquid, and the multiple valves allow for continuous processing of the liquid even when the liquid from one or more containers 14 is spent. In this second embodiment, spent containers may be replaced with new containers of the liquid while the system is processing the liquid from another container. In a third embodiment of the system, at least two inlet valves correspond to each different type of liquid used by the system. This embodiment allows for continuous processing of the liquids, and also allows for the system to process different liquids.

With the appropriate liquid or liquid combination known for processing, the controller determines in step 204 whether the level of liquid in the buffer chamber 20 is "low". If the liquid is "low", in step 206, the controller opens the appropriate inlet valve(s) for delivery of the appropriate liquid or liquid combination. The controller 40 then opens the vacuum valve 24 in step 208, thereby subjecting the buffer chamber 20 to a vacuum. During this time, the bridge valve 28 and the pressure valve 22 are closed. When the buffer chamber is subjected to a vacuum, the vacuum draws liquid from the liquid containers 14 associated with open inlet valves 18. The liquid subjected to the vacuum is drawn from its associated container 14, through the pick-up cap 50 and the associated inlet valve 18 of the inlet manifold 16, and into the buffer chamber 20. During this time, larger bubbles formed in the liquid may be released into the buffer chamber 20. Any such gas bubbles released into the buffer chamber are drawn to the vacuum source and vented out of the system.

After subjecting the buffer chamber 20 to a vacuum, in step 210 the controller 40 continually checks the level of liquid in the buffer chamber until it reaches a "high" level. Once the level of liquid in the buffer chamber reaches "high", the controller closes any open inlet valves in step 212 to end the process of drawing liquid into the buffer chamber.

Next, in step 214, the controller 40 continues to apply a vacuum to the buffer chamber 20 for some period of time after the liquid in the chamber reaches the full level. In one embodiment, this period of time is limited, such as a period of thirty seconds. In the embodiment shown in FIG. 5, this vacuum continues indefinitely until a pressure is applied to the buffer chamber, as described below in step 220. During the time the vacuum is applied to the buffer chamber, gases dissolved in the liquid in the buffer chamber are released from the liquid because of the low-pressure condition within the buffer chamber. These gasses released from the liquid are drawn out of the buffer chamber and into the vacuum source, where they are exhausted from the system. Accordingly, the system provides a degassing process for liquids processed and transferred using the system. In one embodiment, the vacuum applied after the liquid in the chamber has reached the full level is a "high" vacuum that provides an even higher degree of suction to the buffer chamber. This "high" vacuum is advantageous for releasing even further micro gas bubbles from the liquid in the buffer chamber. In this high vacuum embodiment, the microcontroller 40 is operable to control the vacuum source and determine whether a "normal" or "high" vacuum should be applied.

During or immediately after application of the vacuum in step 214, the controller 40 checks the liquid level in the feeder chamber 30 in step 216. If the liquid level is not low, the system returns to step 204 and checks on the liquid level in the buffer chamber 20. If the liquid level in the buffer chamber 20 is not low, the system moves to step 218 and continues to apply a vacuum to the liquid in the buffer chamber in an attempt to further degas the liquid in the buffer chamber. After this, the system again checks the liquid level in the feeder chamber in step 216. Accordingly, the controller is operable to continuously monitor both the buffer chamber and the feeder chamber and take appropriate action to refill such chambers if either chamber becomes low on liquid.

Figure 5:
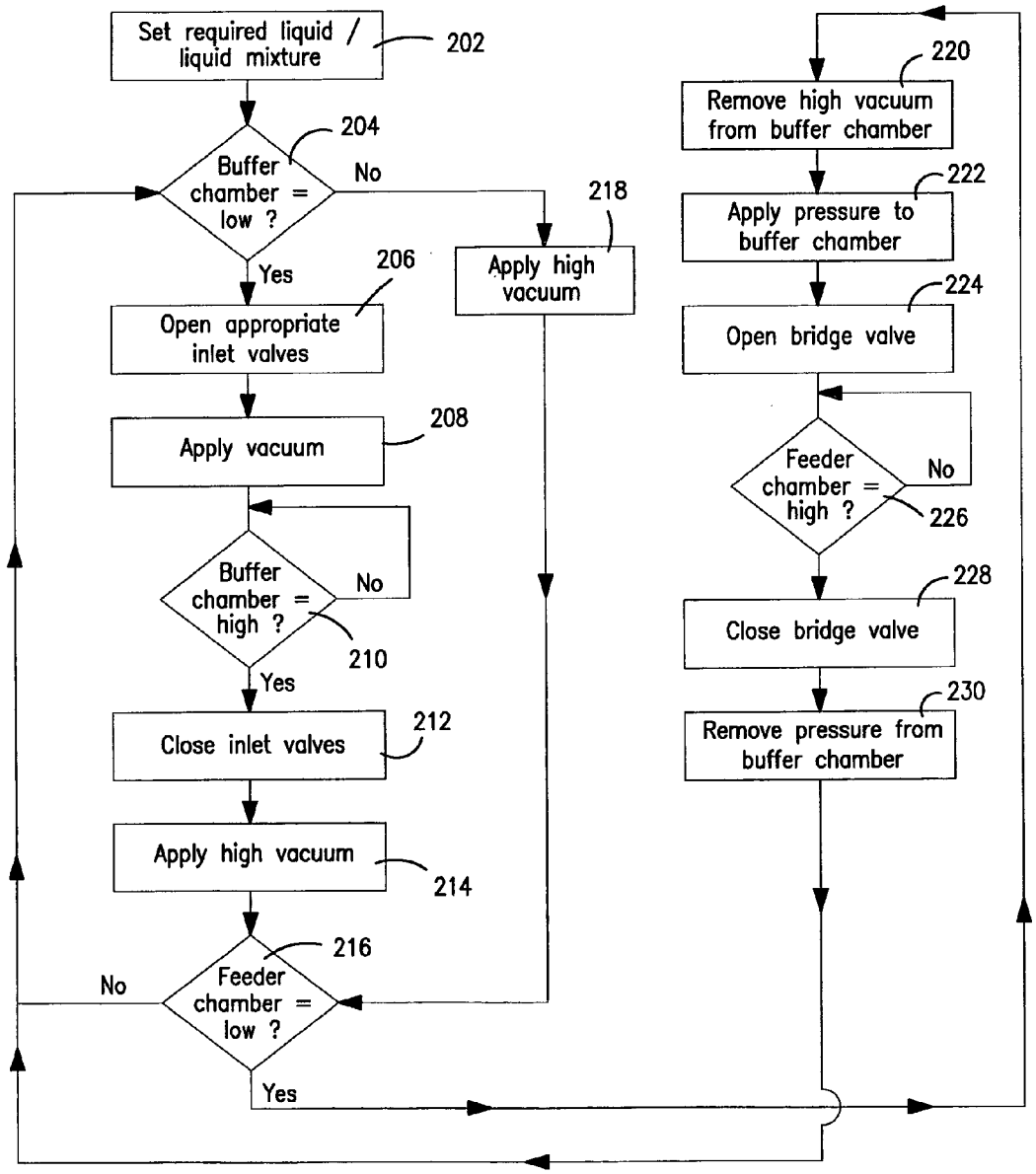
FIG. 5 is a flow chart showing a process used by the system of FIG. 1.

Although not shown in FIG. 5, during the time the controller is checking the level of liquid in the buffer chamber 20 and the feeder chamber 30, the controller 40 is also opening and closing the distribution valves to allow the liquid in the feeding chamber 30 to be distributed to the consuming stations, as needed. Typically, the controller only releases liquid from the feeding chamber to the consuming stations in small increments, such as 1 ml to 5 ml per distribution.

If the sensor of the feeder chamber 30 reports a low liquid level in step 216, the controller 40 immediately removes the vacuum from the buffer chamber 20 in step 220. Then, in step 222, the controller opens the pressure valve 22, causing an increased pressure above atmospheric pressure to be introduced into the buffer chamber 20. Next, in step 224 the controller opens the bridge valve 28, allowing liquid to pass from the buffer chamber 20 to the feeder chamber 30. The increased pressure in the buffer chamber 20 during this time is generally sufficient to force liquid from the buffer chamber 20 to the feeder chamber 30 when the bridge valve 28 is open.

When pressure is introduced into the buffer chamber 20, any remaining micro gas bubbles in the liquid not removed by the vacuum process will dissolve back into the liquid. As mentioned previously, these micro gas bubbles can have negative effects on system measuring apparatus, resulting in false measurements taken by the system measuring apparatus. However, because the liquid is subjected to the buffer chamber 20, significant quantities of micro gas bubbles are removed from the liquid using the system.

In alternative embodiments of the system 10 additional buffer stages and buffer chambers may be added to provide further means for removing micro gas bubbles from the liquid. In these alternative embodiments, only small variations in pressure may be used from stage to stage to discourage dissolution of micro gas bubbles back into the liquid.

With continued reference to FIG. 5, after the controller opens the bridge valve 28 in step 224, the controller monitors the level of liquid in the feeder chamber 30 in step 226 until the sensor in the feeder chamber indicates that the liquid is at a high level. When the liquid in the feeder chamber reaches a high level, the controller 40 closes the bridge valve 28 in step 228. Then, in step 230, the controller closes the pressure valve 22 to remove the pressure from the buffer chamber 20. Then, the controller 40 returns to step 204 to check on the level of liquid in the buffer chamber 20. If the level of liquid is low, the refill process repeats for the buffer chamber 20. If the level of liquid is not low, the controller continues to monitor the buffer chamber 20 and feeder chamber 30 until one of the chambers reaches a low level, indicating that liquid should be transferred into the chamber.

In the manner described above, the system 10 continually keeps adequate amounts of liquid in both the buffer chamber 20 and the feeder chamber 30 so liquid is always available for the next process to be undertaken by the system. With liquid continually available in the feeder chamber 30, the controller 40 is operable to open selective distribution valves 38 in the distribution manifold 32 and feed liquid to the consuming stations whenever needed. Accordingly, the system described herein is operable to continually transfer liquids to multiple consuming stations. In addition, in an alternative embodiment, the system is operable to transfer different liquid reagents to multiple consuming stations at different periods of a system cycle.

Figure 4A:
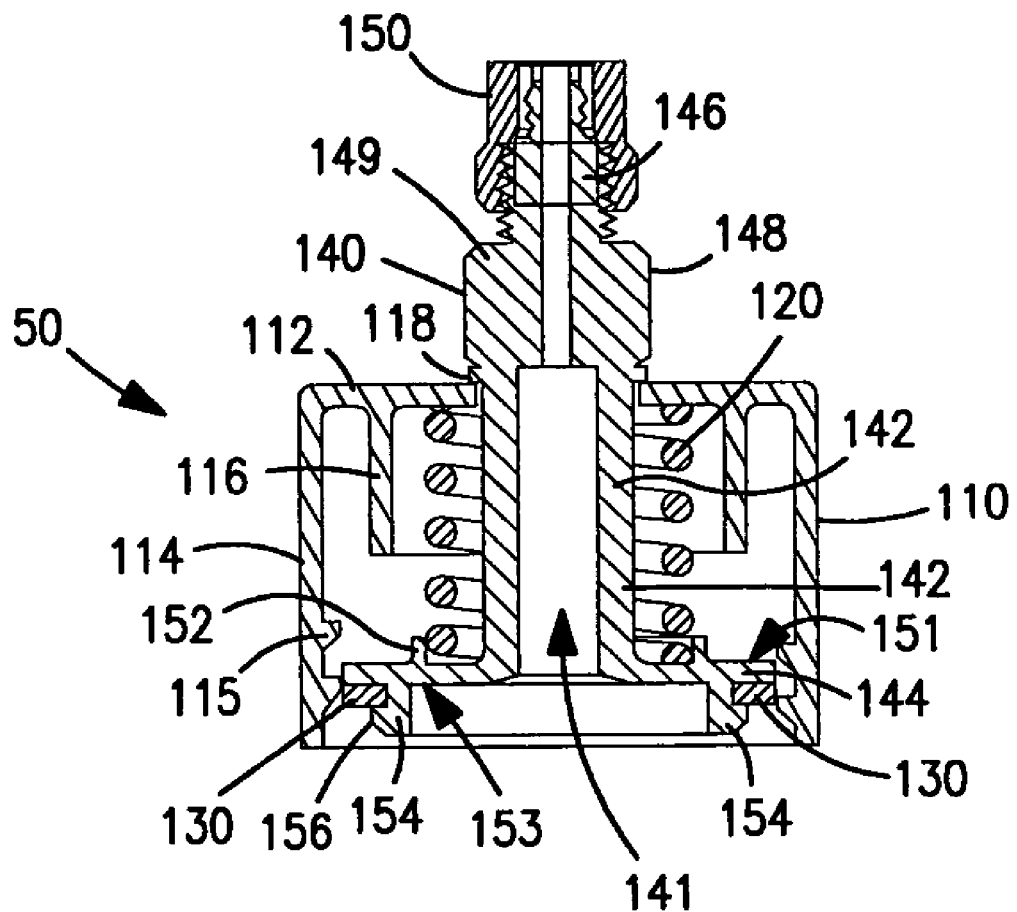
FIG. 4A is a side cross-sectional view of a cap for use with the liquid container of FIG. 3A.

As mentioned previously, the caps 50 are designed to seal to the liquid containers 14. One embodiment of such a cap 50 is shown with reference to FIGS. 4A and 4B. In FIG. 4A, the cap 50 is shown unattached to a liquid container. The cap 50 generally includes a threaded cap portion 110 and a movable plunger portion 140.

The threaded cap portion 110 is generally comprised of a rigid plastic material and includes an upper circular plate 112 with an outer depending skirt 114 and an inner depending skirt 116. A hole 118 is formed in the center of the upper circular plate to allow the plunger to pass through the cap portion 110. The outer depending skirt 114 has a diameter greater than the neck of the collapsible liquid container 14 to which the cap will be attached. The outer depending skirt 114 includes threads 115 near the bottom of an inner wall portion. The threads 115 on the outer depending skirt allow the cap 50 to be screwed on to the mouth of the collapsible liquid container 14.

The inner depending skirt 116 has a diameter that is less than that of the neck of the container 14. The inner depending skirt 116 does not extend as far away from the upper circular plate 112 as the outer depending skirt. As shown in FIG. 4A, the inner depending skirt 116 extends to a length from the upper circular plate 112 such that it is near, but does not reach, the level of the threads 115 on the outer depending skirt 114. A tension spring 120 is retained within the inner depending skirt 116. One end of the spring 120 abuts the upper plate 112 of the cap 50.

The movable plunger portion 140 of the cap 50 includes a head 148, a cylindrical shaft portion 142 and a lower plate 144 attached to the end of the cylindrical shaft portion 142. The head 148 of the plunger 140 includes a top tube connection portion 146 with external knurls, allowing the plunger to be connected to a tube 150. The head 148 also includes a knob portion 149 below the tube connection portion 146. The knob portion 149 has an enlarged diameter that prevents the plunger portion 140 from passing through the hole 118 in the upper plate 112 of the cap portion 110.

The cylinder shaft portion 142 is formed integral with the head 148 and extends between the knob portion 149 of the head 148 and the lower plate 144 of the plunger 140. The cylinder portion 142 is sized to allow the cylinder to pass through the hole 118 in the upper plate 112 of the cap portion 110. A central bore 141 extends through the entire plunger portion 140 in order to allow liquid to pass through the plunger portion 140.

The lower plate 144 is formed integral with the cylindrical shaft portion 142. The lower plate 144 has a diameter substantially equal to the diameter of the neck of the container 14 to which the cap 50 will be sealed. The lower plate 144 includes an upper side/surface 151 and a bottom side/surface 153. The bottom surface 153 along with a first circular wall 154 and lip 156 forms a seal seat adapted to receive and retain the seal 130. The upper surface 151 along with a second circular wall 152 forms a spring seat designed to receive an end of the tension spring 120. With the spring 120 in the spring seat, the spring 120 is trapped between the upper plate 112 of the cap portion 110 and the upper surface 151 of the lower plate 144. This biases the lower plate 144 away from the upper plate 112. However, as mentioned previously, the knob portion 149 is sufficiently sized to prevent the plunger portion 140 from passing entirely through the hole 118 in the cap portion 110.

Figure 4B:
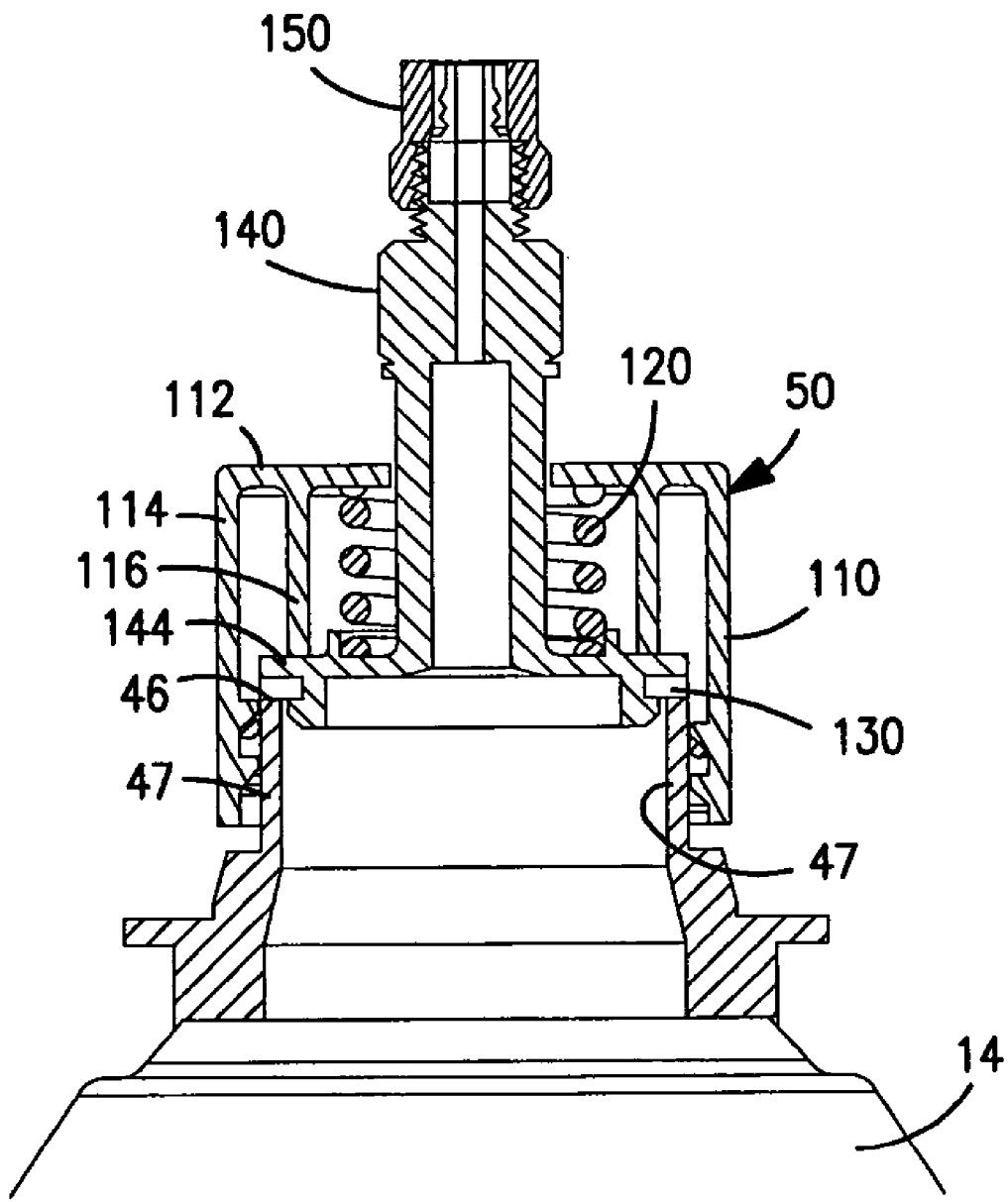
FIG. 4B is a side cross-sectional view of the cap of FIG. 4A attached to the liquid container.

With reference now to FIG. 4B, when the cap 50 is placed on a container 14 and twisted, the threads 115 on the interior of the outer skirt 114 of the cap engage threads on the outer portion of the neck 47 of the liquid container 14. As the threads become further engaged, the cap 50 is secured to the container 14. During this time, the seal 130 of the cap contacts the top rim/mouth 46 on the neck 47 of the liquid container 14. As the cap 50 is twisted on the neck 47, the lower plate 144 is forced toward the upper plate 112, and the spring 120 is compressed. The compressed spring 120 forces the seal 130 to compress against the mouth 46 and form an air-tight seal between the cap 50 and the container 14. Advantageously, the cap 50 need not be fully threaded on the neck 47 of the container 14 for the cap to seal against the container. In particular, the force of the tension spring 120 forcing the disc 144 and seal 130 against the mouth 46 of the container allows for a seal between the cap 50 and container 14 even when the cap is somewhat loose on the container. When the cap 50 is fully twisted and tightened on the container 14, the inner skirt 116 of the cap 50 is forced against the lower plate 144, causing further compression of the seal, and preventing further rotation of the cap 50 on the container 14.

As described above with reference to FIGS. 4A and 4B, a cap 50 is provided that is operable to seal to a liquid container 14. The cap 50 is particularly useful in association with flexible liquid containers as described previously. Because the cap 50 forms a secure seal with the container 14, excess additional air is not allowed to enter the system 10. By preventing additional air from entering the system 10, micro gas bubbles are reduced in liquids transferred and processed using the system. By reducing the amount of micro gas bubbles in the system, the liquids provided by the system produce more accurate and reliable measurements.

Although the present invention has been described with respect to certain preferred embodiments, it will be appreciated by those of skill in the art that other implementations and adaptations are possible. For example, controller operation described herein is but one embodiment of controller operation possible with the system. As another example, the pick-up cap described herein is but one type of cap that may be used with the system. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A liquid transfer system operable to transfer liquid from at least one container to at least one destination, the liquid transfer system comprising:

a) at least one container;
b) at least one liquid input line including at least one valve, wherein the liquid input line leads to the at least one container;
c) at least one vacuum source;
d) at least one destination;
e) a first chamber adapted to retain liquid, the first chamber including
   i) a first liquid inlet port connected to the at least one liquid input line,
   ii) a pressure port connected to the at least one vacuum source, and configured to subject the first chamber to a vacuum, and
   iii) a first liquid outlet port;
f) a second chamber adapted to retain liquid, the second chamber including
   i) a second liquid inlet port,
   ii) a second liquid outlet port connected to the at least one destination, and
   iii) a vent; and
g) at least one liquid output line wherein the at least one liquid output line leads from the first liquid outlet port to the second liquid inlet port;
wherein the at least one valve of the at least one liquid input line is configured to move between an open position and a closed position to control the flow of liquid to the first chamber,
wherein the at least one liquid output line is configured to move between an open position and a closed position to control the flow of liquid to the second chamber, and
wherein the at least one vacuum source is configured to apply a vacuum when the at least one valve of the at least one liquid input line and the at least one liquid output line are in the closed position so as to define a closed system to degas liquid in the first chamber.

2. The liquid transfer system of claim 1 wherein the at least one liquid input line comprises a first portion and a plurality of second portions with an inlet manifold positioned between the first portion and the plurality of second portions, wherein the first portion is connected to the first liquid inlet port of the chamber.

3. The liquid transfer system of claim 2 wherein the inlet manifold comprises a plurality of inlet valves connected to the plurality of second portions of the at least one liquid input line.

4. The liquid transfer system of claim 1 further comprising at least one distribution valve connected to the second liquid outlet port, the at least one distribution valve configured to distribute liquid from the second liquid outlet port to the at least one destination.

5. The liquid transfer system of claim 4 wherein the at least one destination comprises a plurality of liquid consuming stations and the at least one distribution valve comprises a plurality of distribution valves adapted for connection to the plurality of liquid consuming stations.

6. The liquid transfer system of claim 1, further comprising a first sensor, the first sensor comprising a first sensor element and a second sensor element, and wherein the first sensor element is configured to determine if the liquid in the first chamber is above a first low level and the second sensor element is configured to determine if the liquid in the first chamber is above a first high level.

7. The liquid transfer system of claim 6 further comprising a second sensor, the second sensor comprising a third sensor element and a fourth sensor element, wherein the third sensor element is configured to determine if the liquid in the second chamber is above a second low level and the fourth sensor element is configured to determine if the liquid in the second chamber is above a second high level.

8. The liquid transfer system of claim 7 further comprising a bridge valve connected between the first liquid outlet port and the second liquid inlet port.

9. The liquid transfer system of claim 7 further comprising a microcontroller configured to receive an input signal from the first sensor and an input signal from the second sensor, wherein the at least one liquid input line comprises a first portion and a plurality of second portions with an inlet manifold positioned between the first portion and the plurality of second portions, wherein the first portion is connected to the first liquid inlet port of the chamber, wherein the inlet manifold comprises a plurality of inlet valves connected to the plurality of second portions of the liquid input line, and wherein the microcontroller is configured to distribute inlet valve control signals and distribution valve control signals based upon the input signal from the first sensor and the input signal from the second sensor.

10. The liquid transfer system of claim 9 wherein the microcontroller is further configured to distribute a vacuum control signal to the at least one vacuum source.

11. The liquid transfer system of claim 10 wherein the microcontroller is further configured to distribute a bridge valve control signal.

12. The liquid transfer system of claim 1 wherein the at least one liquid input line is sealably connected to the first liquid inlet port and wherein the at least one container is comprised of a flexible body portion.

13. The liquid transfer system of claim 1 further comprising at least one cap configured to seal the at least one liquid input line to the at least one container.

14. The liquid transfer system of claim 13 wherein the at least one cap further comprises
   a) a cap body including an upper plate and a depending skirt, wherein an aperture is formed in the upper plate;
   b) a plunger portion passing through the aperture in the upper plate, the plunger portion including a shaft and a lower plate including an upper side and a bottom side, and a gasket positioned against the bottom side of the lower plate;
   c) a spring positioned between the upper plate and the upper side of the lower plate and thereby biasing the lower plate away from the upper plate.

15. The liquid transfer system of claim 1 further comprising a level sensor positioned in the first chamber, the level sensor configured to determine when the liquid in the first chamber is above a high level.

16. The liquid transfer system of claim 1 further comprising a level sensor positioned in the second chamber, the level sensor configured to determine when the liquid in the second chamber is above a high level.

17. The liquid transfer system of claim 1 further comprising a pressure source, wherein the pressure port is also connected to the pressure source and the pressure source is configured to subject the first chamber to a pressure.

18. The liquid transfer system of claim 10 wherein the microcontroller is configured to receive the input signal from the first sensor when the liquid in the first chamber is above the first high level, and the microcontroller is configured to send an input valve control signal to close the plurality of inlet valves when the input signal from the first sensor is received.

19. The liquid transfer system of claim 18 wherein the microcontroller is configured to send the vacuum control signal to remove the vacuum from the first chamber after delaying for a period of time after receiving the input signal from the first sensor, thereby creating a low-pressure condition within the first chamber and removing gases released by the liquid from the first chamber.

* * * * *